United States Patent [19]
Carrion et al.

[11] Patent Number: 5,965,358
[45] Date of Patent: Oct. 12, 1999

[54] METHOD FOR ASSESSING THE RELATIVE PURITY OF VIRAL GENE TRANSFER VECTOR STOCKS

[75] Inventors: Miguel Carrion; Imre Kovesdi, both of Rockville, Md.

[73] Assignee: GenVec, Inc., Rockville, Md.

[21] Appl. No.: 09/139,000

[22] Filed: Aug. 26, 1998

[51] Int. Cl.[6] .............................. C12Q 1/68; C12Q 1/70; B01D 59/44
[52] U.S. Cl. .............................. 435/5; 435/6; 435/173.9; 250/283; 250/287
[58] Field of Search .............................. 435/235.1, 239, 435/320.1, 5, 173.9, 6; 250/282, 283, 287

[56] References Cited

U.S. PATENT DOCUMENTS

| | | | |
|---|---|---|---|
| 5,486,470 | 1/1996 | Darke et al. | 435/219 |
| 5,605,798 | 2/1997 | Köster | 435/6 |
| 5,696,238 | 12/1997 | Haigwood et al. | 530/412 |
| 5,707,850 | 1/1998 | Cole | 435/239 |
| 5,723,031 | 3/1998 | Dürr et al. | 204/451 |

OTHER PUBLICATIONS

Anonymous, "Probing Viruses with Mass Spec," *R & D Magazine*, p. 33 (Jun., 1998).
Bain et al., *Gene Therapy*, 1,S68 (1994).
Berns et al., *Annals of the New York Academy of Sciences*, 772, 95–104 (1995).
Bothner et al., *J. Biol. Chem.*, 273, 673–76 (1997).
Corman et al., *Biomedical and Environmental Mass Spectrometry*, 19, 646–654 (1990).
Davison et al., *Virology*, 206, 1035–1043 (1995).
Despeyroux et al., *Rapid Communications in Mass Spectrom.*, 10, 937–41 (1996).
Fenselau, *Ann. Rev. Biophys. Biophys. Chem.*, 20, 205–220 (1991).
Fereroff et al., *Proc. Nat. Acad. Sci. USA*, 89, 1636–40 (1992).
Fetzer et al., *Protein Expression and Purification*, 5, 432–441 (1994).
Fink et al., *Ann. Rev. Neurosci.*19, 265–87 (1996).
Gross et al., Spectrom. Online, (May 28, 1998).
Hillenkamp et al., *Biological Mass Spectrom.*, Proceedings of the Second International Symposium on Mass Spectrometry in the Health and Life Sciences, San Francisco, CA, Aug. 27–31, 1989 , 49–60 (1990).
Hillenkamp et al., *Analyt. Chem.*, 63(24), 1193A–1203A (Dec. 15, 1991).
Jurinke et al., *Genetic Analysis: Biomolecular Engineering*, 13, 67–71 (1996).
Maizel et al., *Virology*, 36, 126–136 (1968).
Pepinksy et al., *J. Virology*, 70, 3313–18 (1996).
Siuzdak et al., *Chemistry & Biology*, 3(1), 45–48 (1996).
Siuzdak, *J. Mass Spectrom.*, 33, 203–211 (1998).
Streckert et al., *Intervirology*, 36, 128–133 (1993).
Tas et al., *Biomedical and Environmental Mass Spectrometry*, 18, 757–760 (1989).
Tissue, "Mass Spectrometry Ionization Methods,"Scimedia (http://www.scimedia.com/chemed/ms/ionization.htm) (Nov. 3, 1996).
van der Greef et al., *Biomedical and Environmental Mass Spectrometry*, 16, 45–50 (1988).
Vastola et al., *Organic Mass Spectrometry*, 3, 101–104 (1969).

*Primary Examiner*—David Guzo
*Attorney, Agent, or Firm*—Leydig, Voit & Mayer, Ltd.

[57] ABSTRACT

The present method involves evaluating the purity of a viral gene transfer vector stock by providing an aliquot of the viral gene transfer vector stock and producing charged fragments from the aliquot. The fragments are detected by a detector that produces a sample signal corresponding to the mass-to-charge ratio of the detected fragments. This signal then is compared to a standard signal, whereby the purity of the viral gene transfer vector stock is evaluated.

20 Claims, 1 Drawing Sheet

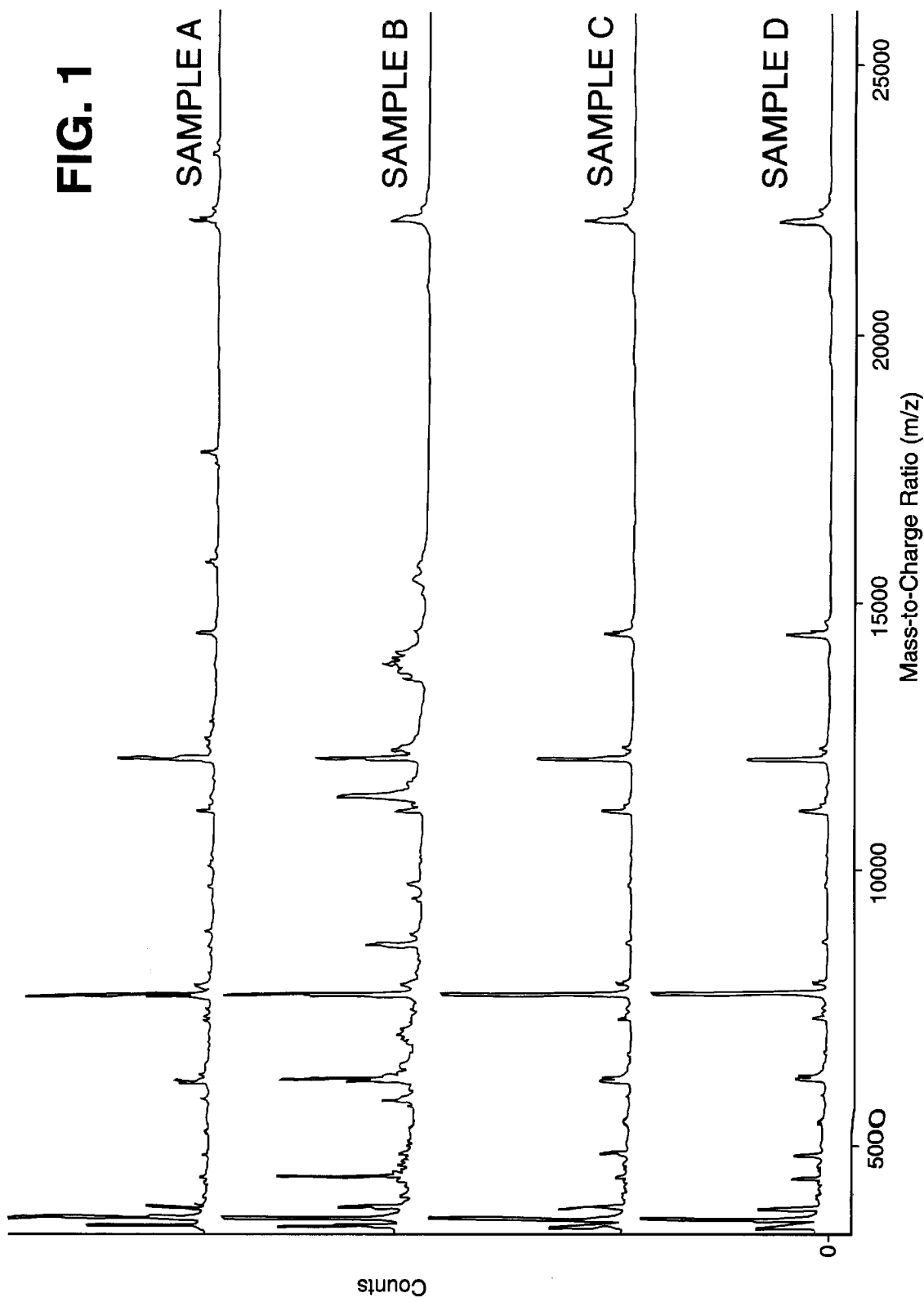

METHOD FOR ASSESSING THE RELATIVE PURITY OF VIRAL GENE TRANSFER VECTOR STOCKS

TECHNICAL FIELD OF THE INVENTION

The present invention relates to methods of assessing the relative purity of stocks of viral gene transfer vectors.

BACKGROUND OF THE INVENTION

Viral gene transfer vectors are widely used throughout molecular biology, especially in gene therapy. A major problem posed by the use of viral gene transfer vectors for gene therapy is the lack of consistent and effective methods to assess the purity of a stock of viral gene transfer vector. The lack of efficient means for determining purity of viral gene transfer vectors has resulted in the inability to measure the effectiveness or consistency of viral gene transfer vector production techniques. These problems are magnified when considering the safety concerns surrounding use of viral gene transfer vectors in human gene therapy.

Traditionally, attempts to measure the purity of an unmodified virus particle in a medium have relied on electrophoresis techniques, such as sodium dodecyl sulfate-polyacrylamide gel electrophoresis (SDS-PAGE), or ultraviolet (UV) spectroscopy measurements. Capillary gel electrophoresis also has been used to analyze viral components in comparison to known standards, as illustrated in U.S. Pat. No. 5,723,031 (Durr et al.) In addition, ultraviolet spectroscopy techniques and ultraviolet resonance spectra have been used to provide structural analyses of several viruses.

Other techniques for assessing viral purity have centered on the use of chromatography techniques such as ion exchange chromatography, gel-filtration chromatography, and reverse phase high performance liquid chromatography (HPLC). For example, researchers have utilized HPLC to purify structural proteins from Herpes Simplex Virus type-1. Similar techniques for purifying viral components have been developed using cation exchange chromatography as described in U.S. Pat. No. 5,486,470 (Darke et al.), ion exchange chromatography as described in U.S. Pat. No. 5,696,238 (Haigwood and Scandella), and electrical chromatography as described in U.S. Pat. No. 5,707,850 (Cole and Gaithersburg).

Mass spectrometry, with the advantage of fast, accurate and detailed analysis as compared to several of the aforementioned techniques, has been used to study individual organic compounds. For example, Vastola et al., *Organic Mass Spectrometry*, 3, 101–104 (1969), disclosed the use of laser pyrolysis mass spectrometry to study the spectra generated by organic salts. Since that time, mass spectrometry has been widely used to evaluate features of larger organic molecules such as proteins. Recently these techniques have been used to study or validate the purity of individual viral proteins or groups of viral proteins such as the components and modifications of viral capsid proteins. For example, Fetzer et al., *Protein Expression and Purification*, 5, 432–441 (1994), teach the use of mass spectrometry in combination with SDS-PAGE to validate the purity of a herpes simplex virus thymidine kinase protein that was subjected to proteolytic cleavage and chromatography purification.

Other researchers have studied groups of viral proteins, for example, Davidson and Davidson, *Virology*, 206, 1035–1043 (1995), disclosed the identification of proteins of channel catfish virus by use of fractionation techniques in combination with laser desorption ionization mass spectrometry. Similarly, Pepinksy et al., *J. Virology*, 70, 3313–18 (1996), used electrospray mass spectrometry to obtain molecular masses for Gag proteins in the Rous sarcoma virus, to study protein intermediates, and to determine that exopeptidase trimming occurred in some of the Gag proteins.

More recently, Bothner et al., *J. Biol. Chem.*, 273, 673–76 (1997), have disclosed the use of matrix assisted laser desorption/ionization mass spectrometry (MALDI or MALDI-MS), in combination with limited proteolysis, upon flock house virus particles to study viral capsid dynamics in that species. Also recently, mass spectrometry has been used as a tool for diagnosing specific DNA molecules in viruses, as described in U.S. Pat. No. 5,605,798 (Koster).

Not until very recently has mass spectrometry been applied to entire virus particles. Tas et al., *Biomedical and Environmental Mass Spectrometry*, 18, 757–760 (1989), met with mixed results in attempting to characterize Vero cell cultures infected with herpes simplex virus and poliomyelitis virus by studying low-weight molecules (i.e., salt molecules, methyl groups, and sugars) that were detected by use of pyrolysis/direct chemical ionization (Py/DCI) mass spectrometry. While Tas et al. suggested that they could possibly identify cell lines infected with a particular virus, they failed to teach a method of obtaining relatively pure viral stocks, especially of a viral gene transfer vector capable of use in molecular biological applications, particularly gene therapy.

Despeyroux et al., *Rapid Communications in Mass Spectrom.*, 10, 937–41 (1996), were able to generate a spectrum for purified cricket paralysis virus (CrPV) by using electrospray ionization mass spectrometry and suggested that comparisons could be made to such spectra. However, Despeyroux et al.'s results are limited because success of their technique was attributed to the small size and simplicity of structural polypeptides of the cricket paralysis virus. Furthermore, similar to Tas et al., Despeyroux et al. failed to teach the combination of such techniques with a useful viral gene transfer vector.

Siuzdak et al., *Chemistry & Biology*, 3, 45–48 (1996), similarly used electrospray ionization (ESI) mass spectrometry, under special settings, to detect viruses. Using standard ESI techniques, Siuzdak et al. were not able to derive signals for large virus particles. Siuzdak et al. were capable of generating signals and performing mass selection on the charged particles from tobacco mosaic virus (TMV) and rice yellow motile virus (RYMV), by using the radio frequency (RF) mode of an ESI mass spectrometer in a manner that retained the ultrastructure of the virus particles. Thus, Siuzdak et al. taught that non-destructive ESI could actually purify virus particles. However, Siuzdak et al. only reported on small viruses (i.e., molecular weights of less than 50,000,000 Daltons), and did not assess the relative purity of a virus that had not been modified by subjection to mass spectrometry.

Siuzdak, *J. Mass Spectrom.*, 33, 203–211 (1998), also disclosed that TOF mass spectrometry might be used to measure large ions such as a whole Tobacco Mosaic Virus. However, such work, if carried out, was not published, and nevertheless would not have provided a method of easily and efficiently assessing relative viral purity, especially in regard to large virus particles, such as with a stock of a useful viral gene transfer vector.

Moreover, many specific types of viral gene transfer vectors that have proven to be powerful tools in molecular biology often have molecular weights well in excess of those of TMV and RYMV. For example, adenoviral vectors, which are useful delivery vehicles, such as in gene therapy, have molecular weights often exceeding 150,000,000 Daltons, three times the weight of the viruses studied by Siuzdak et al.

Furthermore, the techniques taught by Tas et al., Despeyroux et al., and Siuzdak (i.e., ESI and Py/DCI mass spectrometry) are difficult to perform, and require complicated analysis to evaluate their results. Therefore, such techniques may not be a viable alternative for widespread use in the production of viral gene transfer vector stocks.

In view of the state of the art, there remains a need for methods to efficiently evaluate the purity of stocks of viral gene transfer vector. More particularly, there is a need to evaluate the relative purity of stocks of viral gene transfer vectors, suitable for carrying large amounts of genetic information for use in practical biological applications.

BRIEF SUMMARY OF THE INVENTION

The present invention provides a method of evaluating the purity of a viral gene transfer vector stock. The present method of evaluating the purity of a viral gene transfer vector stock comprises providing an aliquot of a viral gene transfer vector stock and producing charged fragments from the aliquot. The fragments are detected by a detector that produces a sample signal corresponding to the mass-to-charge ratio of the detected fragments. This signal then is compared to a standard signal, whereby the purity of the viral gene transfer vector stock is evaluated.

BRIEF DESCRIPTION OF THE DRAWINGS

FIG. 1 is a graph of mass spectrometer traces of various viral gene transfer vector stocks plotted as mass-to-charge ratio (m/z) (x-axis) versus relative counts (y-axis).

DESCRIPTION OF THE PREFERRED EMBODIMENTS

The present method involves evaluating the purity of a viral gene transfer vector stock by providing an aliquot of a viral gene transfer vector stock and producing charged fragments from the aliquot. The fragments are then detected by a detector, which produces a sample signal corresponding to the mass-to-charge ratio of the detected fragments. A standard signal is provided, and the purity of the viral gene transfer vector stock is evaluated by comparing the sample signal to the standard signal.

The present invention is particularly useful in the context of purifying (i.e., substantially enriching a solution comprising) a viral gene transfer vector, for example, a recombinant adenoviral gene transfer vector.

The viral gene transfer vector can be any viral vector that contains at least one exogenous gene. A vector is any polynucleotide competent for introducing one or more exogenous genes into a cellular environment. One skilled in the art will recognize that the viral gene transfer vector (e.g., the viral vector as well as the exogenous gene) can be composed of single-stranded ribonucleic acid (RNA), double-stranded RNA, single-stranded deoxyribonucleic acid (DNA), or double-stranded DNA.

The viral vector can be any vector capable of containing recombinant nucleic acids that are (at least in part) of viral origin. A viral vector as indicated above can be any virus which contains DNA, for example, an adenoviral vector, or one that contains RNA, for example, a retrovirus. Examples of such vectors include, but are not limited to, adenoviral vectors (Bain et al., Gene Therapy, 1, S68 (1994)), adeno-associated viral vectors (Berns et al., *Annals of the New York Academy of Sciences*, 772, 95–104 (1995)), packaged amplicons (Fereroff et al., *Proc. Nat. Acad. Sci. USA*, 89, 1636–40 (1992)), and herpes simplex virus-based viral vectors (Fink et al., *Ann. Rev. Neurosci.*, 19, 265–87 (1996)).

Preferably, a viral vector is a vector derived from viral origin that contains nucleic acid sequences which encode for (a) the production of a capsid, a partial capsid, modified capsid, capsid protein, or modified capsid protein, any of which may or may not have all of the protein sub-units or sub-unit arrangement of the wild-type viral capsid that corresponds to the origin of the viral vector or even identical sub-units to those expressed in the wild-type virus, (b) the functional portion of at least one terminal repeat, for example, the inverted terminal repeats found in adenoviruses or the long terminal repeats found in retroviruses, preferably two functional terminal repeats, including, but not limited to, long terminal repeats (LTRs) or inverted terminal repeats (ITRs) exhibited in viruses which assist in DNA replication, and (c) at least a partial viral packaging sequence, more preferably a sequence that enables the packaging of reproduced viral vector nucleic acids that are about 73% to 110% in size of the corresponding wild type viral genome.

More preferably, the sequences encoding for a capsid, partial capsid, modified capsid, capsid protein(s), or modified capsid protein(s) encode a protein arrangement that substantially shields the viral vector DNA from damage or degradation by enzymatic or other means.

The viral gene transfer vector can have any suitable molecular weight. Viral gene transfer vectors of substantial molecular weights (e.g., the combined mass of proteins, lipids, polysaccharides, and nucleic acids, including the exogenous gene, that comprise the viral gene transfer vector) can be evaluated within the context of the present method. For example, the viral gene transfer vector can possess a molecular weight of at least 1,000,000, 3,000,000, 20,000,000 Daltons, 50,000,000 Daltons, 100,000,000 Daltons, 150,000,000 Daltons, 500,000,000 Daltons, 1,000,000,000 Daltons, or even 1,500,000,000 Daltons.

Similarly, the viral gene transfer vector can have any suitable genome size comprised of nucleic acid sequences or base pair sequences native to the viral vector and those that comprise the exogenous gene. Viral gene transfer vectors of large genomes can be evaluated within the context of the present method. For example, the viral gene transfer vector can have a total genome of at least 2,000 nucleotides or nucleic acid base pairs, 4,000 nucleotides or nucleic acid base pairs, 7,000 nucleotides or nucleic acid base pairs, 20,000 nucleotides or nucleic acid base pairs, 30,000 nucleotides or nucleic acid base pairs, or even 100,000 nucleotides or nucleic acid base pairs.

The exogenous gene in the context of the present invention includes any exogenous nucleic acid that encodes a desired polypeptide or ribonucleic acid, is operatively linked to a suitable promoter, and can be expressed to produce the desired polypeptide or ribonucleic acid. The exogenous nucleic acid is not native to the viral vector, although the promoter operatively linked thereto may or may not be native to the viral vector. Thus, the viral gene transfer vector is not a wild-type virus. The polypeptides or ribonucleic acid encoded by the exogenous nucleic acid can be any suitable polypeptide or ribonucleic acid, such as a reporter polypeptide or ribonucleic acid (i.e., the exogenous gene is a reporter gene), and preferably a therapeutic polypeptide or ribonucleic acid (i.e., the exogenous gene is a therapeutic gene).

The present invention involves the evaluation of a stock of the viral gene transfer vector. The viral gene transfer vector stock can be any composition comprising a viral gene transfer vector and a suitable carrier therefor. The choice of carrier will be determined in part by the particular end use of the viral gene transfer vector stock. The carrier preferably is a pharmaceutically acceptable carrier. A pharmaceutically acceptable carrier typically will be a substance useful in the administration of the viral gene transfer vector to an animal, such as a human, for therapeutic treatment. Pharmaceutically acceptable carriers are known to those skilled in the art and are readily available.

A viral gene transfer vector stock can be produced by transfecting a viral gene transfer vector into a cell (i.e., a production cell) that is permissive for the replication of the viral gene transfer vector to produce a transfected cell. The permissive cell is ordinarily maintained in a medium that promotes cell growth, examples of which are widely known in the art. The transfected cell is maintained in the medium so as to cause the viral gene transfer vector to replicate. The viral gene transfer vector will ordinarily be separated from the cell and from the medium to produce a stock of a viral gene transfer vector.

Preferably, the viral gene transfer vector stock is obtained by infecting eukaryotic cells with a viral gene transfer vector of interest, maintaining the cells for a period of time sufficient to amplify the number of viral gene transfer vector particles, gathering the infected cells together, and lysing (i.e., breaking open) the cells in a buffered solution. The viral gene transfer vector stock can be subsequently treated or modified in any suitable manner. For example, purification or separation techniques can be performed on the viral gene transfer vector stock to remove the viral gene transfer vector from the cells and the medium, thereby yielding a more concentrated stock of the viral gene transfer vector. Such purification and separation techniques are well known in the art. Such techniques can include, but are not limited to, chromatography, electrophoresis, enzymatic or chemical treatment, exposure to heat or radiation, centrifugation, and separation by a differential gradient, for example, a cesium chloride gradient.

The viral gene transfer vector stock can have any suitable level of purification or concentration. For example, the present method can be practiced on unmodified stocks of viral gene transfer vectors which can include undesired substances or molecules, as well as stocks that are considered substantially pure. More specifically, such undesired substances or molecules can include, but are not limited to, the cell, other components of the stock, for example, an undesired buffering agent, and inorganic and organic molecules or polymers, such as biomolecules from the viral gene transfer vector or other living organisms or virus particles, such as nucleic acids, lipids, polysaccharides, and proteins.

The production cell can be any cell permissive of the reproduction of the viral gene transfer vector. The production cell preferably is a eukaryotic cell, more preferably a mammalian cell, and most preferably a human cell. The production cell can be a primary or secondary cell or can originate from a cell line, for example, an immortalized cell line, or a cell line that expresses an immortalized phenotype or characteristics. Such characteristics can be used as a marker, for example, by selecting cells that exhibit such characteristics. Alternatively, or in combination, the production cell can be a cell that expresses a marker gene that allows for either positive or negative selection based upon the expression of the marker gene.

The production cell can have any morphological characteristics that allow reproduction of the viral gene transfer vector in that particular cell. For example, the cell can be epithelial or epithelial-like in morphology, such as cells of, or derived from, human kidney, lung, or neural cells. The cell also can be an embryonic cell, preferably a human embryonic cell, for example, a human embryonic kidney cell, human embryonic lung cell, or human embryonic retinoblast.

The production cell can be a cell that has been modified to express nucleic acids that partially trans-complement the viral gene transfer vector, especially when the viral gene transfer vector otherwise is replication incompetent. For example, the production cell can be a cell that trans-complements a replication incompetent viral gene transfer vector so as to prevent undesired recombination between the genome of the production cell and the viral gene transfer vector, e.g., to prevent a homologous recombination event between the genome of the production cell and the viral gene transfer vector, while allowing the reproduction of the viral vector in the production cell.

An aliquot can be taken from the viral gene transfer vector stock by any suitable technique. Charged fragments (e.g., ionized fragments) are produced from the aliquot by any suitable technique. If desired, the aliquot can be appropriately treated prior to production of the charged fragments therefrom. For example, the aliquot can be treated to reduce the salt level therein (e.g., from a physiological level of 150 mM salt to 50 mM salt or less) to reduce background noise in subsequently detecting the fragments, even if the viral gene transfer vector stock itself will not be so treated, so long as the subsequent comparison of the sample and standard signals is not adversely affected. The present method can be performed using techniques that allow fragmentation without the use of chemical ionization methods. For example, the present technique does not require the use of pyrolysis direct/chemical ionization (PY/DCI) mass spectrometry, or other forms of chemical ionization mass spectrometry, to produce suitable charged fragments.

While the charged fragments can be produced by any suitable technique, the charged fragments typically will be produced by contacting the aliquot with radiation, electrons, or protons, preferably radiation or electrons. Any suitable form of radiation, electrons, or protons can be used in the present method to produce charged fragments from the aliquot. Radiation as used in the context of the present invention refers to the emission of energy in the form of electromagnetic waves, acoustic waves, or particles. Examples of radiation suitable in the context of the present invention include, but are not limited to, radio waves, microwaves, visible light, ultraviolet (UV) light, far UV and infrared rays, x-rays, gamma-rays, infrasonic waves, sonic waves, ultrasonic waves, and $\alpha$- and $\beta$-rays of radioactivity. The electrons can be in any suitable form. For example, the electrons can be in the form of electron beams or individual electrons. Similarly, the protons can be in any suitable form.

The radiation, electrons, and protons can be from any suitable source. For example, radiation can be emitted from a natural source (e.g., radioactive cobalt), an x-ray device, or a laser.

The radiation, electrons, and protons can have any suitable characteristics. In particular, the radiation can have any suitable wavelength. For example, the method can incorporate a radiation pulse that has a wavelength in the infrared spectrum or the ultraviolet spectrum. Similarly, any pulse width suitable to produce fragments can be utilized in the present method. For example, the pulse generated by a laser can have a width of up to about 100, 200, or even 5,000 nanoseconds. Moreover, variable pulse widths and multiple repeated pulses can be used to produce fragments.

The produced fragments can be in any state or quantity suitable for fragment detection. For example, the aliquot can be vaporized at the time the charged fragments are produced from the aliquot, such that the fragments enter into a gaseous or vapor state, have greater mobility, and are subject to easier detection. The fragments can have any suitable velocity at the time of production that allows for detection by the detector. For example, fragments can be accelerated, after they are produced, to a desired velocity before the fragments are detected. The fragments can pass through a field-free region, wherein the velocity of the fragments within the field-free region is proportional to the mass-to-charge ratio of the fragments. One example of such a field-free region is an electric field, particularly an electric field wherein lighter fragments have a higher velocity than heavier fragments. While acceleration of fragments is not required, if the fragments are accelerated, any level of acceleration sufficient for detection of the fragments is suitable. For example, the fragments can be accelerated to a fixed kinetic energy by contacting the fragments with an electric potential.

A viral vector typically will comprise proteins that are associated (or bound) to each other, as well as nucleic acids, which together form the ultrastructure of the viral vector. As a result of contact with the radiation or electrons, the proteins can become disassociated from one another (but otherwise remain substantially intact) and/or the proteins can be further fragmented to yield portions of the proteins. A significant amount of information can be obtained about the viral gene transfer vector stock by fragmenting the individual proteins into portions of the proteins; however, the analysis of such information can be complex and time-consuming. It has been found that the mere disassociation of the viral vector proteins, e.g., merely causing the viral gene transfer vector to lose its ultrastructure through the disassociation of, for example, viral capsid or modified capsid proteins, such that the produced fragments of the viral gene transfer vector comprise, preferably consist essentially of, and more preferably consist of, substantially or entirely intact viral vector proteins typically is sufficient for purposes of present invention and provides information that can be easily and quickly analyzed.

The detection of the produced fragments can be accomplished by any suitable technique. The detection step can include, for example, measuring the time-of-flight for the detected fragments, wherein the time-of-flight is the approximate time required for a fragment to travel a distance across a field-free region. A signal corresponding to the time-of-flight then can be generated.

While the fragmentation and detection steps of the present method can be performed in any suitable manner, they are preferably performed by the use of an analytical device, most preferably by the use of an ion source and a mass analyzer, such as are present in mass spectrometers. Suitable ion sources include electron impact, fast ion or atom bombardment, field desorption, laser desorption, plasma desorption (PD), thermospray (TSP), electrospray ionization (ESI), inductively coupled plasma (ICP), and atmospheric pressure ionization (API). Preferred ion sources include laser desorption, thermospray (TSP), electrospray ionization (ESI), and atmospheric pressure ionization (API). Suitable mass analyzers include quadrupolar analyzers, quadrupole ion trap or quistor analyzers, time-of-flight (TOF) analyzers, magnetic and electromagnetic analyzers, and ion cyclotron resonance analyzers, and fourier transform mass analyzers. The quadrupolar analyzers are preferred, especially in connection with electrospray ionization. The time-of-flight analyzers are more preferable in the context of the present invention, with the most preferred devices for producing and detecting fragments in the context of the present invention being Matrix Assisted Laser Desorption Ionization Time-of-Flight (MALDI-TOF) mass spectrometers. Other mass spectrometers that can be used in the context of the present invention include an electrospray ionization mass spectrometer, a plasma desorption spectrometer, a thermospray ionization spectrometer, and a laser desorption mass spectrometer.

The fragments can have any suitable size for detection and sample signal production and analysis. Relatively large fragments can be detected upon initial fragmentation, without further fragmentation. For example, the produced and detected fragments can have molecular weights of up to 5,000 Daltons, 30,000 Daltons, 150,000 Daltons, or even 300,000 Daltons or more. Thus, multiple fragmentation events can be avoided prior to fragment detection or sample signal production and analysis.

Similarly, the fragments can have any suitable mass-to-charge ratio for detection and sample signal production and analysis. Fragments with relatively large mass-to-charge ratios can be detected, and sample signals produced and analyzed therefor. For example, the produced and detected fragments can have mass-to-charge ratios (m/z) of at least 100, 200, 400, 500, 1,000, 2,500, 5,000, 10,000, 20,000, or even 25,000 or more.

The sample signal generated upon detection of the fragments can be any type of sample signal that allows for comparison to a standard signal. The sample signal can be generated in any suitable manner. Similarly, the standard signal can be any signal and in any form that allows for useful comparison with the sample signal to evaluate the relative purity of the viral gene transfer vector stock. The standard signal can be a single standard signal or a series or group of standard signals indicative of a range of viral gene transfer vector stock purity levels. The sample and standard signals can be associated with any suitable single mass-to-charge ratio and/or any suitable range(s) of mass-to-charge ratios. The sample signal and standard signal can be presented in similar or different (though preferably similar) formats, measurements, or units as long as a useful comparison can be performed. For example, a suitable standard signal can be a signal that is produced from techniques similar to those that are used to generate the sample signal. More specifically, the standard signal can be a signal that is generated from a standard source, e.g., a viral gene transfer vector stock of a known and/or desired relative purity.

The purity of the viral gene transfer vector stock is evaluated by comparing the sample signal to the standard signal in any suitable manner. For example, sample signal and standard signal traces of mass-to-charge ratio versus counts can be compared with respect to the presence, absence, and/or nature of one, some, or all of the peaks of the traces, which differences in the traces reflects the relative purity of the viral gene transfer vector stock.

The present method also can detect and characterize (e.g., identify) one or more contaminants in the viral gene transfer vector stock. For example, the present method can detect and characterize contaminants in the viral gene transfer stock by comparison of the standard and sample signals. The contaminant can have any suitable molecular weight, such as a molecular weight of at least 1,000 Daltons, 3,000 Daltons, 5,000 Daltons, 10,000 Daltons, 30,000 Daltons, 100,000 Daltons, 200,000 Daltons, 500,000 Daltons, or even 1,000,000 Daltons or more. Furthermore, the contaminant can have any suitable mass-to-charge ratio (m/z), such as a mass-to-charge ratio of at least 100, 200, 400, 500, 1,000, 2,500, 5,000, 10,000, 20,000, or even 25,000 or more.

The contaminants can be any suitable type of undesired molecule or composition that can be detected, including, but not limited to, components of the viral gene transfer vector stock. For example, the contaminant can be any organic or inorganic molecule, compound, or polymer, or a portion thereof. More specifically, the contaminant can be a protein, nucleic acid, polysaccharide, or a lipid.

Upon detection of one or more contaminants, the contaminant(s) can be characterized by any suitable technique. For example, the contaminant can be characterized by comparison with the standard signal, or y other techniques such as, but not limited to, subjecting the contaminant to chromatography, differential gradient analysis (e.g., a cesium chloride gradient column or sucrose gradient), mass spectrometry, electrophoresis, centrifugation, or any combination of the aforementioned or other techniques.

Moreover, the contaminant(s) can be removed from the aliquot or viral gene transfer vector stock. This can be accomplished by any suitable technique, such as by any of the techniques referenced above.

Any of the individual steps of the present method can be repeated two or more times. For example, the production of fragments and the detection of the fragments can be repeated two or more times to provide a satisfactory sample signal s). Similarly, multiple viral gene transfer stocks can be provided, an aliquot can be obtained from each such viral gene transfer vector stock, and a sample signal can be produced for each such aliquot, thereby enabling the selection of stocks that have a desired purity based on comparison of the sample signals to the standard signal.

The aliquots can be taken from stocks that have been subjected to sequential cycles of separating the viral gene transfer vector from the production cell and medium. After analysis of the sample signals by comparison with a standard signal, as described above, stocks that have a desired purity can be selected based on the comparison of the sample signals to the standard signal. In this fashion, for example, the viral gene transfer vector stock purification process can be evaluated or "benchmarked."

EXAMPLE

This example further illustrates the present invention but should not be construed to limit the present invention in any way. Although this example is recited using particular embodiments, for example, particular viral gene transfer vector stocks, as well as fragmentation and detection techniques, the skilled artisan will appreciate that the present inventive method can be applied to a wide range of viral gene transfer vector stocks, using a wide variety of techniques as described above.

Specifically, four different adenoviral vector stocks were provided. The adenoviral vector in each stock was an adenovirus of serotype 5 (i.e., Ad5) and contained an exogenous gene. The carrier in each stock was the same and was a physiologically compatible aqueous solution. The adenoviral vector stocks differed as to the manner in which each was purified from the production cells and growth media. The first two adenoviral vector stocks, Samples A and B, were prepared using standard chromatography techniques. The third adenoviral vector stock, Sample C, was prepared using three successive cesium chloride gradients and was considered to represent an adenoviral vector stock of a desirably high degree of purity. The fourth adenoviral vector stock, Sample D, was prepared using a nonconventional anion exchange chromatography matrix technique.

An aliquot was obtained from each of the four adenoviral vector stocks. Each aliquot was treated to reduce its salt concentration, thereby reducing the noise in the subsequent sample signal. Each aliquot was subjected to MALDI-TOF mass spectrometry so as to produce and detect fragments from the aliquot. The mass spectrometry settings were such that the produced fragments comprised substantially intact proteins disassociated from the adenoviral vector, rather than portions of those proteins. The sample signal produced from the detection of the produced fragments resulted in a mass spectrometer trace for each of the aliquots of the four adenoviral vector stocks. These mass spectrometer traces are set forth in FIG. 1 in a graph of mass-to-charge ratio (m/z) (x-axis) versus relative counts (y-axis). Since the third adenoviral vector stock, Sample C, reflected the desired level of purity of the adenoviral vector, the Sample C mass spectrometer trace represented the "standard signal" in accordance with the present invention for purposes of considering the purity of the other adenoviral vector stocks, Samples A, B, and D. The Sample A, B, and D mass spectrometer traces were treated as the "sample signals" in accordance with the present invention.

As is apparent from the mass spectrometer traces of FIG. 1, the fourth adenoviral vector stock, Sample D, is approximately as pure as the "control" adenoviral vector stock, Sample C. The other adenoviral vector stocks, Samples A and B, are not as pure as the "control" adenoviral vector stock, Sample C, with Sample B being less pure than Sample A. This is readily apparent from a comparison of the traces, e.g., the presence, absence, and nature of the peaks of the traces.

In the Sample C "standard signal," the peaks at, for example, approximately 11000, 12000, and 14500 mass-to-charge ratios (m/z) are quite sharp. This is also true with respect to the Sample D "sample signal" as compared to the Sample C "standard signal." Moreover, there are no significant additional or missing peaks in the Sample D "sample signal" as compared to the Sample C "standard signal." This similarity of the Sample D "sample signal" and the Sample C "standard signal" reflects a similar degree of purity of the adenoviral vector stocks.

In contrast, the peaks at approximately 11000, 12000, and 14500 mass-to-charge ratios (m/z) are much broader in the Sample A and Sample B "sample signals" as compared to the Sample C "standard signal." Moreover, there are significant additional peaks in the Sample A "sample signal" at, for example, approximately 17500 and 23000 mass-to-charge ratios (m/z), and in the Sample B "sample signal" at, for example, approximately 11500 and 13500 mass-to-charge ratios (m/z), as compared to the Sample C "standard signal." In addition, there are significant missing peaks in the Sample A and Sample B "sample signals" at, for example, 4500 mass-to-charge ratio (m/z), as compared to the Sample C "standard signal." This lack of similarity of the Sample A "sample signal" and the Sample C "standard signal," and the even greater lack of similarity of the Sample B "sample signal" and the Sample C "standard signal," reflect the presence of a higher level of contaminants in those adenoviral vectors stocks (i.e., adenoviral vector stocks of lower purity), more so with respect to Sample B than Sample A, as compared to the "control" adenoviral vector stock Sample C.

Thus, it is readily apparent from the results of this example that the present invention is quite useful in assessing the relative purity of viral gene transfer vector stocks.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments can be used and that it is intended that the invention can be practiced otherwise than as specifically described herein. Accordingly, this invention includes all modifications encompassed within the spirit and scope of the invention as defined by the following claims.

What is claimed is:

1. A method of evaluating the purity of a viral gene transfer vector stock, the method comprising:
   (a) providing an aliquot of a viral gene transfer vector stock;
   (b) producing charged fragments from the aliquot;
   (c) detecting the fragments by a detector which produces a sample signal corresponding to the mass-to-charge ratio of the detected fragments;
   (d) providing a standard signal; and
   (e) evaluating the purity of the viral gene transfer vector stock by comparing the sample signal to the standard signal.

2. The method of claim 1, wherein the fragments pass through a field-free region, wherein the velocity of the fragments within the field-free region is proportional to the mass-to-charge ratio of the fragments.

3. The method of claim 1, wherein steps (b) and (c) are repeated two or more times.

4. The method of claim 1, wherein steps (b) and (c) are performed by a mass spectrometer selected from the group consisting of an electrospray ionization mass spectrophotometer, a plasma desorption spectrophotometer, a thermospray ionization spectrophotometer, and a laser desorption mass spectrophotometer.

5. The method of claim 1, wherein steps (b)–(d) are performed by Matrix Assisted Laser Desorption Ionization Time-of-Flight (MALDI-TOF) spectrophotometry.

6. The method of claim 1, wherein providing an aliquot of a stock of a viral gene transfer vector in step (a) of the method comprises:
   (a1) transfecting a viral gene transfer vector into a cell that is permissive for the replication of the viral gene transfer vector to produce a transfected cell, wherein the cell is in a medium;
   (a2) maintaining the transfected cell in the medium so as to cause the viral gene transfer vector to replicate;
   (a3) separating the viral gene transfer vector from the cell and from the medium to produce a stock of a viral gene transfer vector; and
   (a4) obtaining an aliquot from the stock.

7. The method of claim 1, wherein the viral gene transfer vector is an adenoviral vector.

8. The method of claim 1, wherein the viral gene transfer vector comprises proteins associated with each other, and the fragments of the viral gene transfer vector comprise substantially intact proteins disassociated from the viral gene transfer vector.

9. The method of claim 1, wherein the comparison of the sample signal to the standard signal in step (e) further comprises the step of detecting the presence of a contaminant in the viral gene transfer vector stock.

10. The method of claim 1, wherein the viral gene transfer vector has a molecular weight at least 100,000,000 Daltons.

11. The method of claim 1, wherein the viral gene transfer vector is a vector that contains more than 4,000 nucleotides or nucleic acid base pairs.

12. The method of claim 1, wherein the sample signal comprises a signal produced from a fragment having a molecular weight of up to 300,000 Daltons when the fragment is detected.

13. The method of claim 1, wherein the sample signal comprises a signal produced from a fragment having a mass-to-charge ratio of at least 200 when the fragment is detected.

14. The method of claim 1, wherein the standard signal is provided by a viral gene transfer vector stock of known purity.

15. The method of claim 2, wherein the detection of the fragments in step (c) further comprises:
   (c1) measuring the time-of-flight for the detected fragments, wherein the time-of-flight is the approximate time required for a fragment to travel a distance across the field-free region; and
   (c2) producing a sample signal corresponding to the time-of-flight.

16. The method of claim 6, wherein the method further comprises:
   (a5) repeating steps (a3) and (a4) a desired number of times to obtain a series of viral gene transfer vector stocks and aliquots thereof;
   (f) performing steps (a)–(e) on each aliquot obtained in step (a5) to produce a set of sample signals; and
   (g) selecting stocks that have a desired purity based on the comparison of the sample signals to the standard signal.

17. The method of claim 8, wherein the fragments of the viral gene transfer vector consist essentially of substantially intact proteins disassociated from the viral gene transfer vector.

18. The method of claim 9, wherein the method further comprises the characterization of the contaminant.

19. The method of claim 9, wherein the method further comprises the step of removing the contaminant from the viral gene transfer vector stock.

20. The method of claim 14, wherein the standard signal is provided by:
   (a) providing an aliquot of a viral gene transfer vector stock of known purity;
   (b) producing charged fragments from the aliquot; and
   (c) detecting the fragments by a detector which produces a standard signal corresponding to the mass-to-charge ratio of the detected fragments.

* * * * *